United States Patent [19]
Rogozinski

[11] Patent Number: 5,947,968
[45] Date of Patent: Sep. 7, 1999

[54] GRAFT ANCHOR AND METHOD

[76] Inventor: Chaim Rogozinski, 3223 Front Rd., Jacksonville, Fla. 32217

[21] Appl. No.: 09/094,502

[22] Filed: Jun. 10, 1998

Related U.S. Application Data

[63] Continuation-in-part of application No. 08/962,838, Nov. 30, 1997.
[51] Int. Cl.$^6$ .................................................. A61B 17/56
[52] U.S. Cl. ............................... 606/61; 606/60; 606/72; 606/73; 623/17
[58] Field of Search ................... 606/60, 61–75; 623/17–23

[56] References Cited

U.S. PATENT DOCUMENTS

| | | | |
|---|---|---|---|
| 5,360,429 | 11/1994 | Jeanson et al. | 606/61 |
| 5,545,164 | 8/1996 | Howland | 606/61 |
| 5,649,925 | 7/1997 | Barbera Alacreu | 606/61 |

*Primary Examiner*—Michael Buiz
*Assistant Examiner*—Lien Ngo
*Attorney, Agent, or Firm*—Edward S. Irons

[57] ABSTRACT

An anchor for immobilizing a spinal bone graft in position for fusion to adjacent vertebrae is described. The anchor may be used as a component of a spinal implant system as described in U.S. Pat. No. 5,716,357.

7 Claims, 5 Drawing Sheets

5,947,968

GRAFT ANCHOR AND METHOD

RELATED APPLICATIONS

This application is a continuation-in-part of application Ser. No. 08/962,838 filed Nov. 30, 1997 for "Spinal Implant and Method" which is incorporated herein by reference.

FIELD OF INVENTION

This invention relates to means and methods for anchoring spinal bone grafts such as disc replacements. More particularly, the invention relates to means and methods for anchoring bone grafts in vertebral fusion position between spaced apart longitudinal components of a spinal implant system.

BACKGROUND OF THE INVENTION

The spinal column generally comprises thirty three vertebrae whose ends articulate by interposed pads of discs or cartilaginous tissue. On occasion, such discs are replaced by bone grafts which, in time, fuse to the ends of adjoining vertebrae.

Known spinal fixation implants may include generally parallel elongate members and associated transverse connectors. See, e.g., U.S. Pat. Nos. 5,522,816 and 5,688,272. Spinal implant systems which comprise longitudinal members composed of a chain of interconnected links which may be cross-connected at a distal end are described in U.S. Pat. No. 5,716,357. The links may be in the form of plates or rods with a central portion and end portions apertured for attachment to vertebrae by bone bolts or like means. The apertured end portions may be offset from the central portion such that a portion of the graft area is exposed upon implantation. The exposed graft area provides greater surgeon accessibility to the bone graft site and optimization of the graft bed and of useful graft volume.

There is a need for means and a method to immobilize or anchor bone grafts in proper position on exposed anterior portions of a vertebra or vertebrae as fusion proceeds.

SUMMARY OF THE INVENTION

This invention provides means and a method for anchoring one or a plurality of grafts in fusion position on the anterior portions of vertebrae. One specific embodiment of the invention may comprise imnmobilizing a bone graft in position for fusion on a vertebra by anchor means which overlays and which may be secured to the graft. The anchor means may also be secured to a longitudinal component of a spinal implant positioned adjacent to a portion of the spine, including a vertebra on which the graft is anteriorly positioned.

A particular embodiment of this invention is a means for spanning an exposed exterior surface of a graft and secured to at least one of two spaced part longitudinal link constructs, such as the link constructs 101, 102 shown by FIG. 2 of this application.

Another aspect of the invention may comprise a method for immobilizing a spinal bone graft which comprises securing anchor means to the potentially exposed graft surface, positioning said graft properly positioned for fusion on an anterior surface of a vertebra, and thereafter securing said anchor means to an implanted longitudinal member, thereby immobilizing said graft in fusion position.

DESCRIPTION OF THE PREFERRED EMBODIMENTS

The graft anchor means and method of the invention are useful in conjunction with any spinal implant system that includes a longitudinal element secured to adjacent vertebrae. The preferred embodiments of the invention are designed for use with spinal implant systems as shown generally by FIG. 2, including longitudinal members comprising a plurality of links secured in chain-like fashion for implantation in generally parallel relationship on opposite sides of the spine.

The invention is now described by reference to the Figures.

Figure 1:
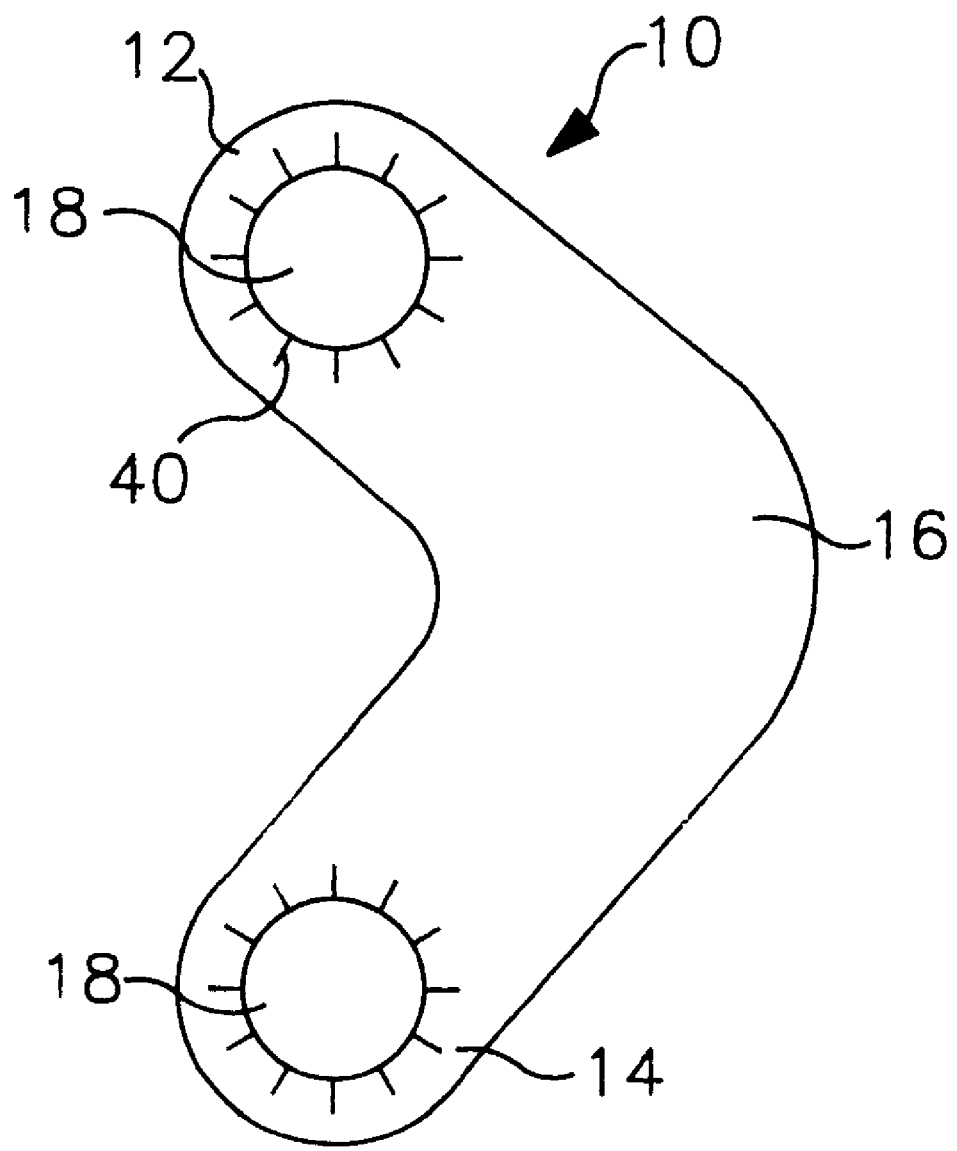
FIG. 1 (prior art) is a reproduction of FIG. 1A of U.S. Pat. No. 5,716,357, a front elevational view of one spinal implant link member having apertured end positions offset from a central portion. Links which are not offset, as shown for example by FIGS. 4A, 4B and 4C of application Ser. No. 08/962,838, and longitudinal chains of such links may also be used.

In FIG. 1, a link member is indicated generally by the reference numeral 10, which includes first and second end portions 12, 14 and a central portion 16. Each of the end portions 12, 14 has an aperture 18 configured to receive a threaded bone bolt or screw to secure the link 10 to adjacent vertebrae. The links 10 are preferably integrally formed so as to comprise a one-piece structure. The surface of the links adjacent the end portion apertures may have radial cuts or other interdigitating structure for facilitating and enhancing the locking engagement of the links with a bone bolt or screw.

The end portions 12, 14 of the links 10 are offset from the central portion 16 as in links 10, 20 and 30. This offset is such that a line passing through the midpoint of the apertures formed in the end portions of links 10, 20 and 30 does not overlie the central portion of the link. See the dashed line in FIG. 2.

Figure 2:
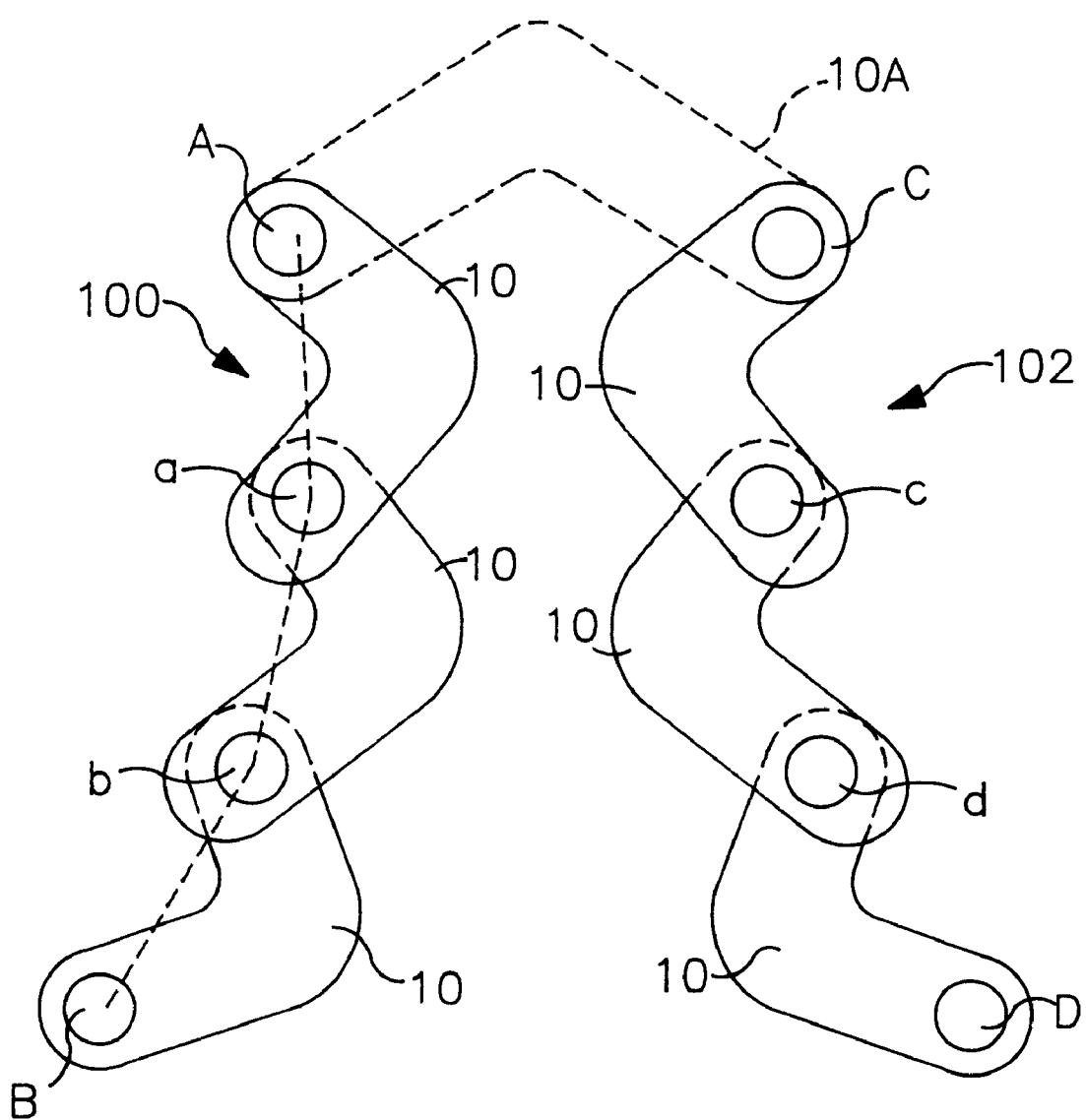
FIG. 2 (prior art) is a reproduction of FIG. 4 of U.S. Pat. No. 5,716,357, a front elevational view showing a plurality of link members as depicted in FIG. 1 placed together in two longitudinal, generally parallel chain-like constructs 101, 102.

The generally parallel rigid constructs 100 and 102 as shown in FIG. 2 are formed of a plurality of link members 10 interconnected in chain-like fashion. The links 10 are positioned with the end of one link overlying the end of an adjacent link. With respect to the construct 100 (on the left hand side of FIG. 2), a line passing through the midpoints of connection points A, a, b and B does not follow a linear path. The same is true with regard to the construct 102 and connection points C, c, d and D.

Figure 3:
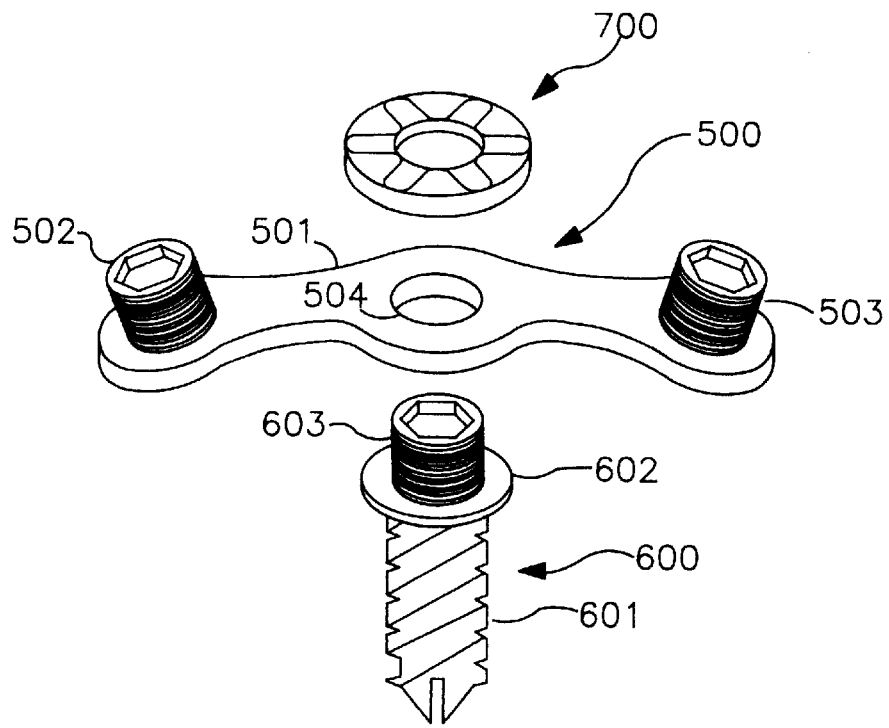
FIG. 3 is an exploded view which depicts parts of one form of a graft anchor assembly of this invention. A graft anchor 500, a bone bolt 600 for securing the anchor to a graft and a locknut 700 (similar to locknut 400 (FIG. 9) of application Ser. No. 08/962,838) are shown.

FIG. 3 illustrates a graft anchor 500, a bone bolt 600 and a locknut 700. The graft anchor 500 comprises an elongated member shown in the form of a plate 501 having upwardly extending threaded means 502 and 503, preferably of a length to accommodate two links 10, and a centrally disposed aperture 504. The bolt 600 comprises a threaded bone engaging portion 601, a shoulder 602 and an upwardly extending threaded portion 603 for passage through the aperture 504 of the graft anchor 501. Locknut 700 is for engagement of the threaded portions 502 and 503 of the graft anchor 500 and the threaded portion 603 of the bone bolt extending upwardly from the graft anchor 501 after passage through the aperture 504. Bone bolts or screws and locknuts, for example as described in U.S. Pat. No. 5,716,357 or pending application Ser. No. 08/962,838, may be used. However, the invention may include the use of other forms of bone bolts, screws or locknuts as may be desired.

Figure 4:
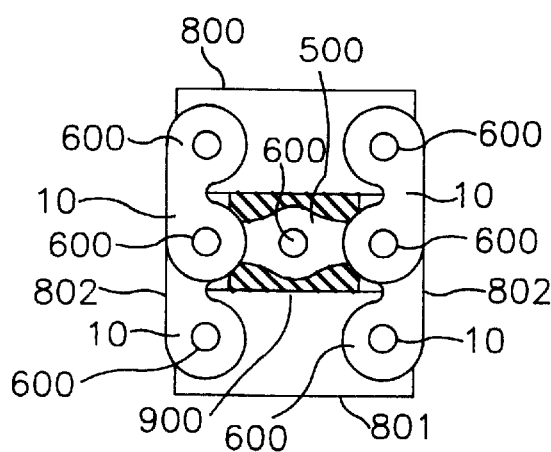
FIG. 4 is a schematic depiction of a single graft anchor assembly of the invention secured to adjacent portions of longitudinal chains of offset links as shown generally by elements 100, 102 of FIG. 2. Two vertebrae and one bone graft are schematically illustrated.

FIG. 4 is a schematic depiction of two vertebrae 800 and 801 interconnected by two chains 802 of links 10 secured anteriorly to the vertebrae 800–801 by bone bolts 600 or the like and secured by locknut 700. A bone graft 900 is shown positioned for fusion between the vertebrae. The graft anchor 500 transversely connects the two link chains 802 and overlays the otherwise exposed portion of bone graft 900.

Figure 5:
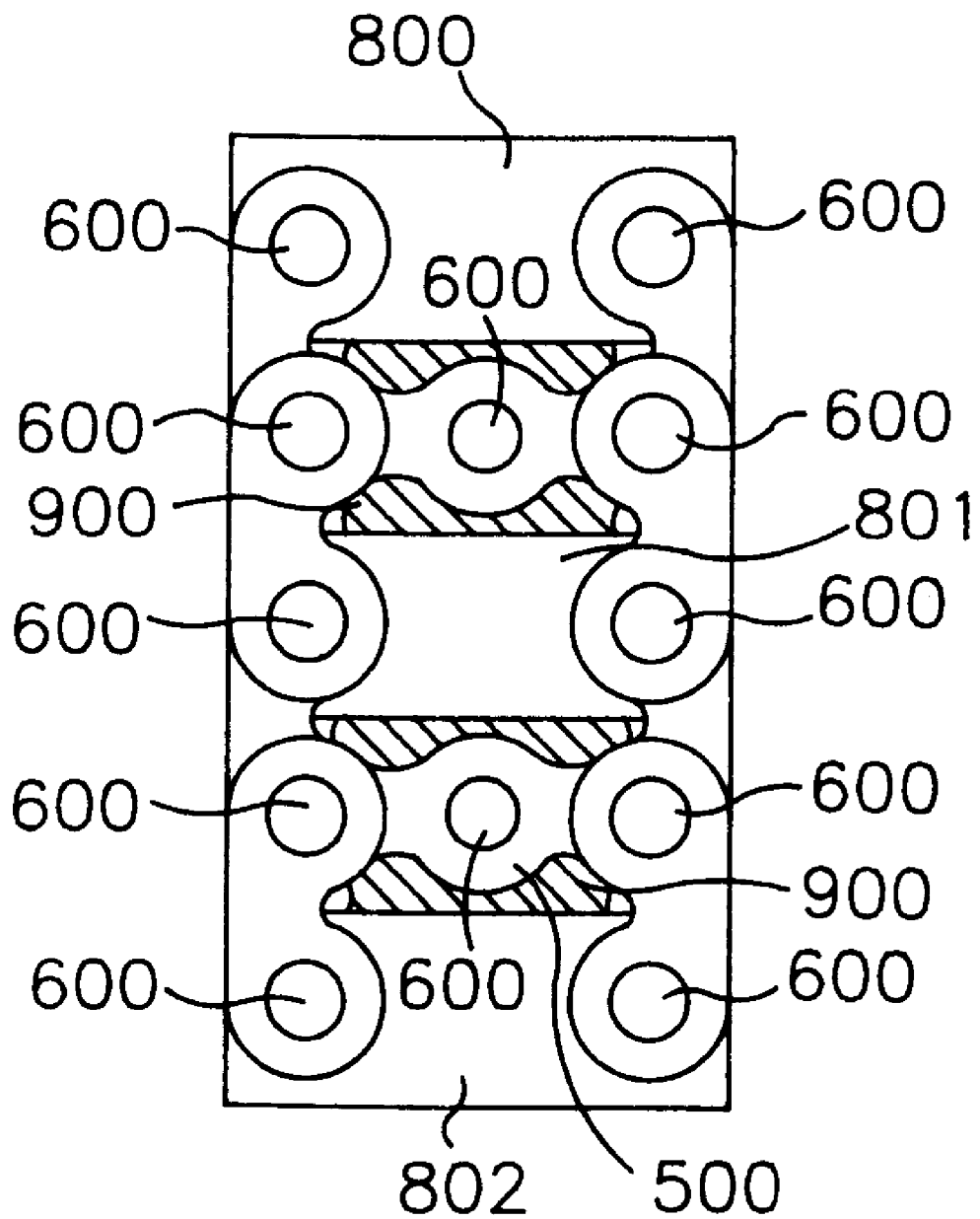
FIG. 5 is a schematic depiction of two graft anchors, each in an installed assembly similar to that shown by FIG. 4. Any desired or necessary number of graft anchors may be implanted in like manner.

A plurality or series of bone grafts may be concurrently utilized in like manner as shown by FIG. 5. FIG. 5 illustrates two bone grafts 900 positioned for fusion between three vertebrae 800, 801 and 802.

Figure 6:
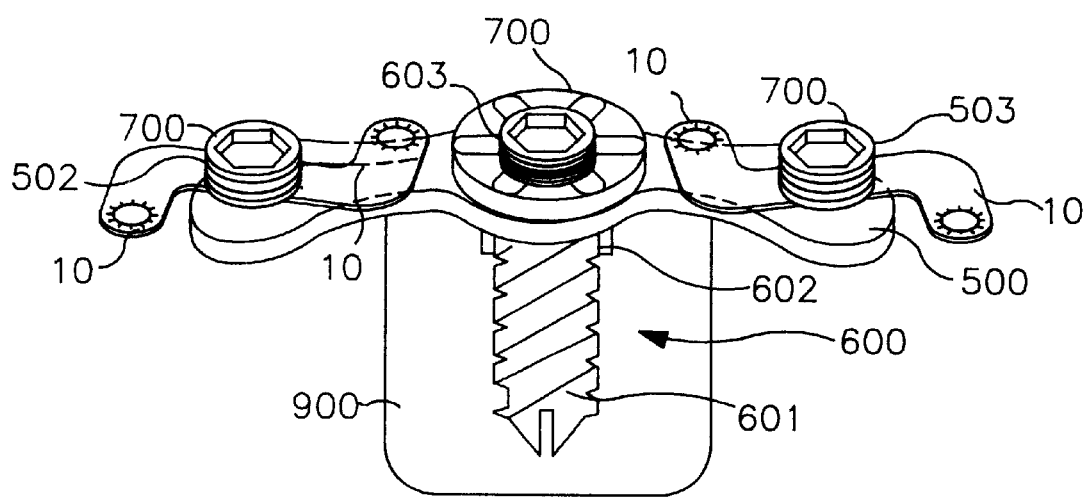
FIG. 6 is a schematic view in section of one graft anchor implantation pursuant to the invention.

FIG. 6 is a schematic that shows, in cross-section, a single graft anchor after installation in the manner generally indicated by FIG. 4.

Those skilled in the art will appreciate the method for use of the graft anchor from the preceding description and the figures. One preferred method includes, as a first step, securing the graft anchor element to the graft to provide an anchor and graft assembly. As a second step, an implant including a longitudinal element comprising a plurality of link members (see FIG. 2) is installed adjacent the portion of the spine selected to receive the graft. In the installation process, the implant engaging elements 502 and 503 of the graft anchor included in the anchor graft assembly are passed through the bone screw apertures of links from which the longitudinal element is constructed. The graft anchor is secured in position by locknuts 700 or the like.

I claim:

1. A spinal bone graft anchor which comprises:
   (i) an elongated member for spanning an exposed upper surface of a spinal bone graft,
      wherein said elongated member has a first end portion, a second end portion, and a central portion between said first and second end portions, and
      wherein said elongated member has a lower surface for contact with said exposed upper surface of said bone graft,
   (ii) means for engaging an element of a spinal implant at each of said first and second end portions of said elongated member, and
   (iii) means in said central portion of said elongated member for securing said elongated member to said bone graft.

2. The claim 1 spinal bone graft anchor, wherein said means for engaging an element of a spinal implant comprises a threaded means extending upwardly from said elongated member.

3. The claim 1 or claim 2 spinal graft anchor, wherein said means for engaging an element of a spinal implant comprises means for engaging at least one of a plurality of link members interconnected in chain-like fashion to form a longitudinal element of a spinal implant system.

4. In a spinal implant system comprising two generally parallel longitudinal members for attachment to adjacent vertebrae, wherein said longitudinal members are an assembly of link members secured in chain-like fashion, the improvement which comprises
   a spinal bone graft anchor means wherein said bone graft anchor means comprises:
      (i) an elongated member having a first end portion, a second end portion, and a central portion for spanning the exposed upper surface of a spinal bone graft positioned between said two generally parallel longitudinal means, and
      (ii) means at said first end portion or said second end portion for securing said bone graft anchor means to at least one of said parallel longitudinal members.

5. The claim 4 spinal implant system, wherein said spinal bone graft anchor means further comprises means for securing said anchor means to said bone graft.

6. The claim 5 spinal implant system, wherein said means for securing said anchor means to said bone graft comprises an aperture in the mid-portion of said anchor means to accommodate a bone bolt for insertion into said bone graft.

7. A spinal implant system comprising:
   (i) two generally parallel, spaced apart longitudinal members for attachment to opposite sides of vertebrae
      wherein a spinal bone graft having an exposed upper surface may be positioned for fusion between said spaced apart longitudinal members, and
   (ii) bone graft anchor means for spanning said space between said spaced apart longitudinal members above and in contact with said exposed surface of bone graft
      wherein said bone graft anchor means comprises opposite end means for securing said bone graft anchor to each of said longitudinal members.

* * * * *

UNITED STATES PATENT AND TRADEMARK OFFICE
CERTIFICATE OF CORRECTION

PATENT NO.    :  5,947,968
DATED         :  September 7, 1999
INVENTOR(S)   :  Chaim Rogozinski It is certified that error appears in the above-identified patent and that said Letters Patent is hereby corrected as shown below:

On the titla page:
   Item [63] on title page should read:  --[63] Continuation-in-part of application No. 08/962,838, Nov. 3, 1997.--

Signed and Sealed this

Eighteenth Day of April, 2000

Attest:

Q. TODD DICKINSON

Attesting Officer

Director of Patents and Trademarks